United States Patent
Herskowitz et al.

[11] Patent Number: 6,130,183
[45] Date of Patent: Oct. 10, 2000

[54] CATALYST FOR OXIDATIVE DEHYDROGENATION OF PARAFFINIC HYDROCARBONS AND USE OF THIS CATALYST

[75] Inventors: Mordechay Herskowitz, Meitar; Miron Landau; Mark Kaliya, both of Beer-Sheva, all of Israel

[73] Assignees: Mannesmann Aktiengesellschaft, Düsseldorf, Germany; K.T.I. Group B.V., AB Zoetermeer, Netherlands

[21] Appl. No.: 08/860,934

[22] PCT Filed: Dec. 15, 1995

[86] PCT No.: PCT/DE95/01840

§ 371 Date: Jul. 9, 1997

§ 102(e) Date: Jul. 9, 1997

[87] PCT Pub. No.: WO96/22161

PCT Pub. Date: Jul. 25, 1996

[30] Foreign Application Priority Data

Jan. 18, 1995 [DE] Germany .......................... 195 02 747

[51] Int. Cl.[7] .......................... B01J 27/06; B01J 27/138; B01J 23/00; B01J 23/16; B01J 23/06; C07C 5/373; C07C 5/333

[52] U.S. Cl. .......................... 502/349; 502/224; 502/226; 502/227; 502/302; 502/303; 502/304; 502/340; 502/344; 502/350; 502/352; 502/353; 585/658; 585/661

[58] Field of Search .......................... 502/224, 226, 502/227, 302–304, 340, 344, 350, 352, 353; 585/658, 601

[56] References Cited

U.S. PATENT DOCUMENTS 3,743,683 7/1973 Croce et al. .......................... 260/680
4,774,216 9/1988 Kolts et al. .......................... 502/174
5,118,899 6/1992 Kimble et al. .......................... 585/500

Primary Examiner—Marian C. Knode
Assistant Examiner—Thuan D. Dang
Attorney, Agent, or Firm—Cohen, Pontani, Lieberman & Pavane

[57] ABSTRACT

Disclosed is a novel catalyst and process using the novel catalyst for the oxidative dehydrogenation and cracking of $C_2$ to $C_5$ paraffins (homogeneous hydrocarbons or mixtures such as liquified gas to $C_2$ to $C_5$ olefins in the presence of an oxygen-containing gas and water vapor. The novel catalyst has the following formula $$X_a Y_b Z_c A_d O_x,$$

where, referring to the Periodic System,

X is an element of Group II and/or IV b (Mg, Ca, Za, Ti, Zr . . . )
Y is a Lanthanide and/or an element of Group IVa or Va (Ce, La, Nd, Dy, Sn, Pr, Sb, Pb . . . );
Z is an element of Group I (Li, Na, K . . . );
A is an element of Group VII (Cl, Br, I . . . );
O is oxygen; and
a is 0.4 to 0.9,
b is 0.005 to 0.3,
c is 0.05 to 1.5,
d is 0.05 to 0.8, and
x is determined by the valance requirements of metals and halogens.

The catalyst is used in the form of pressed spherical pellets or extrudates with added binder or deposited on a carrier material of one of the aforementioned oxidic components or of a separate carrier material. The weight-related space velocity, relative to the hydrocarbons used, is in the range of 0.1 to 20 $h^{-1}$ and the temperature is 400 to 700° C.

27 Claims, No Drawings

CATALYST FOR OXIDATIVE DEHYDROGENATION OF PARAFFINIC HYDROCARBONS AND USE OF THIS CATALYST

FIELD OF INVENTION

The invention relates to a process for the oxidative dehydrogenation (and cracking as secondary reaction) of $C_2$ to $C_5$ paraffinic hydrocarbons (pure hydrocarbons or mixtures, such as liquified petroleum gas-LPG) to $C_2$ to $C_5$ olefins, wherein a novel catalyst, which is distinguished by high paraffin conversion and high olefin selectivity, is used.

BACKGROUND OF INVENTION

U.S. Pat. No. 4,524,236 discloses a process for the oxidative dehydrogenation (oxydehydrogenation) of ethane, in which a calcined composition of the elements Mo, V, Nb, Sb as the catalyst [sic] and X=Li, Sc, Na, Be, Mg, Ca, Sr, Ba, Ti, Zr, Hf, Y, Ta, Cr, Fe, Co, Ni, Ce, Zn, Cd, Hg, Al, Tl, Pb, As, Bi, U, W, Te is used. This catalyst provides a conversion of up to 73% at a selectivity of 69% for ethylene at 400° C. and a weight-related space velocity (WHSV) of 1.5 $h^{-1}$. The abovementioned patent states that the catalyst, because it does not efficiently oxydehydrogenate propane, n-butane or i-butane, but instead combusts these gases to carbon dioxide and other oxidized carbon products, is essentially limited to the oxydehydrogenation of ethane to ethylene.

The article "Selective Oxidation of Methane and Ethane of Li⁻—MgO-Cl⁻ Catalysis Promoted with Metal Oxides" by S. J. Conway, D. J. Wang and J. H. Lunsford in Applied Catalysis A79, pp. L1 to L5 (1991) discloses catalysts for the oxydehydrogenation of ethane to ethylene that include magnesium oxide and lithium oxide, chlorine and other metals from the La, Nd and Dy group. This catalyst [sic] provides a conversion rate of 83.8% for ethane with a selectivity for ethylene of 63.8% at a temperature of 585° C. and a WHSV of 0.18 $h^{-1}$. No further information is available about the performance of this catalyst in the oxydehydrogenation of LPG components.

U.S. Pat. No. 1,777,319 discloses a vanadium-based catalyst for the oxydehydrogenation of $C_2$ to $C_8$ paraffins at temperatures of 300 to 700° C. The formula of the catalyst is $M_3(VO_4)_2$ and/or $MV_2O_6$, where M is one of the elements Mg, Zn, Ca, Pb or Cd. The inventors of this catalyst disclose detailed information in later articles.

In these articles, "Selective Oxidative Dehydrogenation of Butane over V—MG—O Catalysts" by M. A. Chaar, D. Partel, M. C. Kung and H. H. Kung journal of Catalysis 105, pp. 483–498, 1987), "Selective Oxidative Dehydrogenation of Propane over V—MG—O Catalysts" by M. A. Chaar, D. Partel and H. H. Kung journal of Catalysis 109, pp. 463 to 467, 1988) and "Selectivity Patterns in Alkane Oxidation over $Mg_3(VO_4)_2$ to MgO, $Mg_2V_2O_7$ and $(VO)_2P_2O_7$" by P. M. Michalakos, M. C. Kung, I. Jahan and H. H. Kung journal of Catalysis 140, pp. 226 to 242, 1993), the authors disclose mixed oxide catalysts that contain vanadium and magnesium. The catalysts are active at temperatures in the range of 475 to 540° C. for the oxydehydrogenation of propane, butane and isobutane. At 540° C. and WHSV=2 $h^{-1}$, conversion is achieved for butane at a level of up to 58.9% and for propane of 35.8%. At 500° C. and WHSV= 6.5 $h^{-1}$, conversion of 12% is achieved for isobutane with a selectivity for corresponding olefins and butadiene of 48.8% and 42.4% and 53.0%. No information is available about the conversion of LPG over V—MgO catalysts. Based on the data for the pure components, it can be concluded that for LPG containing roughly 50% propane, a conversion of 40% and a selectivity of 50% can be achieved with an olefin yield of roughly 20% per passage at WHSV=2 $h^{-1}$. This was confirmed by tests carried out in the framework of studies for the present invention.

An important feature of these V—Mg catalysts is the high selectivity of the oxydehydrogenation path. No cracking reactions were observed. Another feature of these catalysts is that the main product of the dehydrogenation of n-butane is butadiene, whereby the selectivity for $C_4H_6$ is 37.7%, with a total selectivity of 48.8%, and the yield of butadiene, among all dehydrogenation products, is 77.2%.

The article by D. Bhattacharyya, S. K. Bej and M. S. Rao, "Oxidative Dehydrogenation of n-Butane to Butadiene. Effect of Different Promoters on the Performance of Vanadium-Magnesium Oxide Catalysts" (Applied Catalysis A87, pp. 29 to 43, 1992), discloses a mixed oxide catalyst that consists of a mixture of vanadium, magnesium and a third component made from Mo, Cr and Ti or Cr and Ti. At 570° C. and WHSV=0.8 $h^{-1}$, this catalyst provides a conversion of 59% and a selectivity of 53% with a yield of oxydehydrogenation products of 33.8%, of which 70% is butadiene.

Studies for the present invention have shown that, in contrast to the catalyst known from U.S. Pat. No. 4,524,236, the Li—Mg—X—Cl catalyst known from Applied Catalysis A79, pp. L1 to L5 (1991), which was developed for the oxydehydrogenation of ethane, has a high selectivity in LPG conversion for olefins at 600° C. and WHSV=0.18 $h^{-1}$. An increase in WHSV for the LPG causes a drastic reduction in LPG conversion: At WHSV=1 $h^{-1}$ and 600° C., the conversion was 10.9%, with roughly the same selectivity of 80%.

Further features of this Li—Mg—X—Cl catalyst are the partial cracking of butane, propane and isobutane under the conditions of oxydehydrogenation, whereby corresponding low olefins and methane are obtained, and negligible amounts of butadiene in the oxydehydrogenation products.

In summary, it can be said that according to the available data, the best catalyst allows a high LPG conversion with low selectivity to be achieved for olefins at a WHSV of roughly 2 $h^{-1}$ (V—Mg—O basis catalyst) or a high selectivity for olefins with a low conversion at a WHSV>1 $h^{-1}$ (Li—Mg—X—Cl basis catalyst).

The object of the present invention is to provide a novel catalyst and a process using this catalyst for the oxidative dehydrogenation (and cracking) of $C_2$ to $C_5$ paraffins to $C_2$ to $C_5$ olefins at high conversion rates and simultaneously with high selectivity for olefins.

SUMMARY OF THE INVENTION

The present invention provides a process and an oxidic catalyst for the oxidative dehydrogenation and cracking of $C_2$ to $C_5$ paraffins (homogeneous hydrocarbons or mixtures such as LPG) to $C_2$ to $C_2$ to $C_5$ olefins in a gaseous phase. The catalyst is calcined and has a composition in accordance with the formula $X_a\ Y_b\ Z_c\ A_d\ O_x$, where:

X=Element of Group 11 [sic] and/or IVb (Mg, Ca, Ti, Zr . . . )

Y=Element of the group of lanthanides and/or the Groups IVa of Va [sic] (Ce, La, Nd, Dy, Sn, Pr, Sb, Pb)

Z=Element of Group I (Li, Na, K . . . )

A=Element of Group VII (Cl, Br, I . . . ) and a=0.4 to 0.9 b=0.005 to 0.3 c=0.05 to 1.5 d=0.05 to 0.8 x=a number determined by the valance requirements of the metals and halogens.

The values of a, b, and c determine the relative mole fractions of the elements X, Y, Z and A in the catalyst. The elements other than the halogens are present in combination with oxygen in the form of various oxides or as halogenides.

The invention also includes the manner of producing the catalyst as pressed, roughly spherical pellets, or as extrudates with an added binder, or on a carrier, whereby the carrier consists of one of the oxidic components of the catalytic material alone or with the added binder or of a separate carrier material. The invention is characterized by the catalyst and encompasses the operating conditions of temperature T, pressure P, and weight-related space velocity (WHSV), the mole ratio of oxygen to hydrocarbons, the addition of an inert gas or water, special measures for maintaining catalyst stability, and conveyance to a fixed bed reactor or a moving bed reactor.

PREFERRED EMBODIMENT

Just as the choice of components to be used can have a significant influence on the performance of a catalyst, so too can the special process used to produce and activate the catalyst. The elements of the catalyst composition are present in combination with oxygen or halogens as oxides or halogenides. Preferably, the catalyst is produced from a solution of the soluble components, which include the Z and A components, and from the insoluble powdered oxides of the X and Y components. The Y components can also be introduced in the form of soluble compounds. The solution is preferably a hydrous system at pH 1 to 12 and above, and preferably at pH 3 to 6. The temperature can be 20 to 100° C. As a rule, a mixture of the compounds that contain the elements is prepared by dissolving an adequately large quantity of the soluble compounds and dispersing the insoluble compounds to produce the desired mol ratio of the elements in the catalyst. The catalyst is then obtained by removing the water or other solvent from the solution at a temperature in the approximate range of 70 to 100° C. The moist catalyst is dried at 110 to 150° C., preferably at 130° C., in air or in oxygen over a period of 10 to 24 hours. An increase in temperature shortens the synthesis time. The dry solid substance is ground into a powder with a grain size of 400 to 800 μm. Calcination is preferably carried out in several steps. In the first step, calcination is carried out in air or oxygen at temperatures of 250 to 600° C., preferably at approximately 400° C. for a period of 0.5 to 5 hours, preferably 2 hours. This is followed by additional calcination at a temperature of 620 to 850° C., preferably 750° C., over of period of 10 to 24 hours.

The material is pressed and formed into small spheroids using added moisture and surface-active substances and plastification or is shaped by extrusion using an added binder. The group of binders that can be used for the catalyst includes the oxides of silicon, aluminum, zirconium, titanium, hafnium and mixtures thereof. In a further calcination step, the catalyst pellets, in the form of spheroids or extrudates, are calcined in air or oxygen at temperatures of 620 to 850° C., especially preferably at approximately 750° C., over a period of 10 to 24 hours to obtain the desired catalyst composition. This sequence of heat-treatment steps is preferred, although the catalyst can also be produced with a calcination step at 620 to 850° C. prior to shaping. In that case, the catalyst is produced by impregnation of a suitable carrier material. In accordance with the process described above, calcination is first carried out in the temperature range of 250 to 600° C. and then in the temperature range of 620 to 850° C.

Silica and alumina, in particular, can be used as the carrier material for the catalyst, as can silicon carbide, silicon nitride and, especially preferably, one of the aforementioned X or Y components in oxidic form, or mixtures of these substances with or without binders. When a binder that contains neither X nor Y components is used, the actual catalytic material accounts for approximately 10 to 90% of the weight of the catalyst, while the remainder consists of the carrier material or binder. It is advisable to introduce titanium, zirconium or hafnium into the solution in the form of oxides (powder or pellets). These components can also be added to the catalytic composition in the form of hydroxides, which, mixed with other aforementioned inert binders, serve as the binder. Preferably, the lanthanides (cerium, lanthanum, neodymium, dysprosium, praseodymium), tin, antimony and/or lead are introduced into the solution in the form of insoluble powdered oxides. Other water-soluble compounds of elements of the sort that can be used include suitable nitrates, halogenides or oxalates. The preferable alkali components are Li, Na and/or K. These are introduced in the form of water-soluble nitrates or halogenides. The elements Cl, Br and/or I are preferable as halogens, and are added in the form of water-soluble ammonium salts.

The catalyst is preferably produced in the general manner described below:

The Z components that are nitrates or halogens are dissolved in water and form a first clear solution. The A components that are ammonium salts are dissolved in the first solution, so that a second clear solution is formed. The X components that are oxides are mixed with the second solution to form a first suspension. The Y components that are oxides are introduced into the first suspension, so that a second suspension is created. On the other hand, the Y compounds that are soluble nitrates or halogenides are partially dissolved in the second solution. After the second suspension is mixed and heated for a period of approximately 15 minutes at a temperature of approximately 80° C., the water is evaporated. Preferably, this is done in a vacuum during continuous stirring (in a rotary evaporator), so that rapid drying is achieved. However, drying can also be carried out in air. When the catalyst is produced on a carrier, it is advantageous to carry out the impregnation with separate, clear, filtered solutions of the Y, Z and A component compounds in a step-by-step manner with intermediate drying steps, to avoid precipitation in the impregnation solution.

The size and activity of the surface of the catalyst depend on the extraction time, i.e., on the time spent to evaporate the second suspension to dryness. Compositions that can leach out for a relatively long time (e.g., 30 minutes or longer) prior to drying at 130° C. generally experience grain growth with a loss in surface size. When the catalyst is to be used in the form of extrudates, the evaporated material, after being dried at e.g. 130° C. and calcined at e.g. 500° C., is mixed with aluminum oxide, titanium oxide and/or zirconium oxide and/or with colloidally distributed silica (silica sol), by means of the addition of a desired quantity of nitric acid (or ammonia, in the case of a silica binding agent) [sic], plastified by the addition of polyethylene glycol, cellulose or other burn-out compounds and extruded through an apertured plate with subsequent drying and calcination.

The catalyst according to the invention should contain one or more metal components shortly below their highest-possible oxidation step. Calcination is carried out as an oxygen-containing gas is passed via the dry solids obtained from the suspension in order to control the reduction activity of the reduction agent, e.g., $NH_3$ or organic reduction agents that were introduced into the system for the plastification and shaping into pellets. The throughput rate of the gas can be determined experimentally for the calcination device and quantities of solids used, in order to optimize the properties of the catalyst to be produced. One or more free valances of the metals in the catalysts are occupied by one or more oxides and halogenides. Generally, the catalyst (extruded, or with or without carrier material) can be used in a fixed bed reactor or a moving bed reactor.

The process according to the invention is described in greater detail below.

Possible loading materials are ethane, propane, butane, isobutane and pentane as well as their mixtures in various compositions from any desired sources. The gas flow can also contain considerable quantities of carbon monoxide, nitrogen, methane, ethane, ethylene and $C_3$ to $C_5$ alkenes, each with more than 5% by volume, as well as water in the form of water vapor. In general, the reaction mixture used to carry out the process is as follows: 1 mol $C_2$ to $C_5$ paraffins, 0.05 to 2.0 mol molecular oxygen (either as pure oxygen or in the form of air or another oxygen-containing gas), 0 to 5 mol nitrogen, 0.1 to 5 mol dilution agent for the reaction, preferably water vapor, and 0 to 0.01 mol halogens (Cl, Br or I) in the form of organic halogenides (chloroform, dichlorethane, etc.). Water vapor is used both as the dilution agent and as a heat moderator for the reaction, and also serves as a reactant to improve the olefin yield. The halogens are used as stabilizers to prevent deactivation of the catalyst. At high reaction temperatures, halogens can evaporate from the solid. This requires the addition of halogens to the loading material. Other gases, e.g., helium, carbon dioxide and methane, can also be used as the dilution agent or heat moderator for the reaction. Water leads to the formation of a certain amount of butyraldehyde, acrylaldehyde and acetaldehyde from the produced olefins. Their quantity does not exceed a value of 5%.

The gaseous reaction mixture is evenly mixed before being introduced into the reaction zone. The components can be preheated, individually or after mixing prior to their introduction, into the reaction zone, which should have a temperature of from 400° C. to approximately 700° C. The pressure in the reaction zone is approximately 1 to 5 bar and the temperature is 400 to 700° C., preferably 520 to 650° C. and most preferably 580 to 640° C. The WHSV calculated on the basis of the paraffin flow is in the range of 0.1 to 20 $h^{-1}$, and preferably in the range of 1 to 4 $h^{-1}$. Generally, the process is carried out in a single step, whereby the total oxygen for the reaction is added together with the dilution agent. It is desirable to performs the process without an inert dilution agent, such as nitrogen, so that separating the produced olefins is facilated. When no dilution agent is used, certain problems may arise. The large quantity of oxygen can create hazardous conditions, which favor an explosion and a reduction in the selectivity of the process for olefins. Implementing the process in multiple steps makes it possible to introduce the oxygen required for the entire reaction of the paraffin in different steps so os to avoid the creation of potentially hazardous conditions.

The invention is explained further in reference to the following examples. The tests were carried out in a tubular reactor using various catalysts and under the following conditions:

The composition of the supplied gas mixture was 20% by volume LPG (50% by volume propane, 25% by volume butane, 25% by volume isobutane) or individual $C_3$ and $C_4$ paraffins, 20% by volume oxygen and 60% by volume water in the form of water vapor. The WHSV of the paraffin was roughly 6 $h^{-1}$ at a total pressure of 1 bar. The reactor consisted of a quartz tube 15 mm in diameter, which was heated in an electric oven. The temperature in the isothermal zone, where the catalyst was arranged between two layers of quartz particles, was approximately 590° C. The reactor contained 1 g of the catalyst, which was mixed with 5 g quartz particles. The water and traces of liquid products were condensed in a condensation device at −20° C.

The gaseous products were analyzed. In all cases, the percentages of hydrocarbon conversion (X) and olefin selectivity (S) were calculated as follows:

$$X = 100 - \Sigma C_{pi}$$

$$S = \Sigma C_{oi}/X * 100\%$$

where $C_{pi}$ and $C_{oi}$ are the percentages by weight of the paraffins and olefins in the hydrocarbon mixture at the reactor output.

EXAMPLE 1

A catalyst with the following composition was produced:

$Zr_{0.62}Dy_{0.04}Li_{0.46}Cl_{0.24}O_x$

A quantity of 4.23 g lithiurrf nitrate was added to 150 ml water, heated to 80° C. and stirred for 15 minutes to obtain a first clear solution. A quantity of 2.3 g ammonium chloride was added to the first solution at 80° C. and stirred for 20 minutes to obtain a second clear solution. A quantity of 1.0 zirconium oxide (baddeleyite) was added to the second solution and stirred at 80° C. for 10 minutes to obtain a first suspension. A quantity of 1.0 g dysprosium oxide was added to the first suspension and stirred at 80° C. for 15 minutes to obtain a final suspension. The water in the final suspension was evaporated while being stirred continuously. The moist solid was dried at room temperature, broken, sifted to a grain size fraction of 400 to 800 $\mu$m, and dried overnight in an oven at 130° C. The dried material was calcined in an oven at a temperature of 500° C. for two hours in flowing air. The temperature was then increased to 750° C. for 16 hours. The calcined material was cooled in a cooling room, crushed and pressed into pellets of 2.5×0.5 cm. The pellets were crushed, sifted to a particle size of 400 to 800 $\mu$m and again calcined in air at 750° C. for 16 hours. The catalyst was tested for the oxidative dehydrogenation of a paraffin mixture in accordance with the process described above. The results are shown in Table 2.

EXAMPLE 2

Using the method described in Example 1, a catalyst with the following composition was prepared:

$Zr_{0.61}Dy_{0.08}Li_{0.43}Cl_{0.15}O_x$

The same quantities were used as in Example 1, except that 2.0 g dysprosium oxide was used, so that the produced catalyst had a higher dysprosium content than the catalyst in Example 1. The results of the test of this catalyst in the oxidative dehydrogenation of an LPG mixture are shown in Table 2.

EXAMPLE 3

Using the method described in Example 1, a catalyst with the following composition was produced:

$Zr_{0.62}Dy_{0.04}Li_{0.86}Cl_{0.28}O_x$

The same quantities were used as in Example 1, except that 8.46 g lithium nitrate was used, so that the produced catalyst had a higher lithium content than the catalyst in Example 1. The results of the test of this catalyst in the oxidative dehydrogenation of an LPG mixture are shown in Table 2.

EXAMPLES 4 to 10

Examples 4 to 10 were carried out using the same method as in Example 1 and with the same quantities of the X, Y, Z and A components in g-atom. The elements of the X, Y, Z and A components varied. Table 1 shows the X, Y, Z and A components, the X, Y, Z and A salts or oxides, the weights of the X, Y, Z and A salts or oxides and the composition of the catalysts for Examples 4 to 10. The results of the tests with these catalysts are shown in Table 2.

After drying at 110° C. and calcination at 550° C., the pellets were calcined again at 750° C. for a period of 15 hours.

All examples show the high efficiency of the new catalyst, which is expressed in the high conversion rates of the paraffinic hydrocarbons and the high selectivity for olefins. The yield of olefins is remarkably high and reaches values above 40% (compared with 20 to 30% in conventional processes). In addition, the process according to the invention is implemented at relatively low temperatures and under almost isothermal conditions. This results in a significant reduction in energy consumption.

The invention is not limited by the embodiments described above which are presented as examples only but can be modified in various ways within the scope of protection defined by the appended patent claims.

TABLE 1

| | X | | Y | | Z | | A | | Catalyst Composition | | | |
|---|---|---|---|---|---|---|---|---|---|---|---|---|
| Ex # | Salt | Wgt/g | Salt | Wgt/g | Salt | Wgt/g | Salt | Wgt/g | | | | |
| 4 | $TiO_2$ | 6.5 | $Dy_2O_3$ | 0.75 | $LiNO_3$ | 3.2 | $NH_4Cl$ | 2.3 | Ti 0.55 | Dy 0.03 | Li 0.35 | Cl 0.21 |
| 5 | $ZrO_2$ | 10.0 | $La_2O_3$ | 0.22 | $NaNO_3$ | 2.66 | $NH_4Br$ | 3.7 | Zr 0.60 | La 0.01 | Na 0.24 | Br 0.21 |
| 6 | $ZrO_2$ | 10.0 | $Nd_2O_3$ | 0.23 | LiCl | 1.22 | $NH_4Cl$ | 2.3 | Zr 0.60 | Nd 0.01 | 2Li 0.22 | Cl 0.45 |
| 7 | $TiO_2$ | 7.1 | $Pr(NO_3)_3$ | 0.90 | KCl | 9.70 | $NH_4Cl$ | 2.3 | Ti 0.60 | Pr 0.02 | K 1.00 | Cl 0.50 |
| 8 | $ZrO_2$ | 10.0 | $Dy(NO_3)_3$ | 0.47 | $LiNO_3$ | 2.30 | $NH_4I$ | 8.8 | Zr 0.60 | Dy 0.02 | Li 0.25 | I 0.34 |
| 9 | $TiO_2$ | 7.1 | Sn(II)oxalate | 6.56 | $NaNO_3$ | 3.32 | $NH_4Cl$ | 2.3 | Ti 0.60 | Sn 0.20 | Na 0.30 | Cl 0.26 |
| 10 | $ZrO_2$ | 10.0 | Sb(II)oxalate | 5.00 | $LiNO_3$ | 3.90 | $NH_4Br$ | 6.7 | Zr 0.60 | Sb 0.15 | Li 0.42 | Br 0.38 |

EXAMPLE 11

A catalyst produced using the method described in Example 1 was tested in the oxidative dehydrogenation of propane under the conditions described above. The conversion of propane was 79%; the selectivity for $C_2$ to $C_3$ olefins was 61%.

EXAMPLE 12

A catalyst produced according to the method described in Example 1 was tested in the oxidative dehydrogenation of isobutane under the conditions described above. The conversion of isobutane was 77%; the selectivity for $C_2$ to $C_4$ olefins was 59%.

EXAMPLE 13

By depositing a portion of the active oxides on an extruded carrier material (2.5 mm diameter), which comprised $ZrO_2$ and $Al_2O_3$ (the latter as binder), a catalyst of the following composition was produced:

$Zr_{0.62}Dy_{0.012}Li_{0.14}Cl_{0.18}O_x$—$Al_2O_3$ 13 g Zr hydroxide pellets, which were coextruded with Al hydroxide (Product 706/03 of MEL Chemicals), were calcined at 550° C. in air for 5 hours to dehydrogenate both hydroxides. After calcination, the carrier material contained 85% by weight $ZrO_2$ and 15% by weight $Al_2O_3$.

15.5 g Dy $(NO_3)_3$×5 $H_2O$ and 27.5 g $LiNO_3$ were dissolved in 30 g water at room temperature. The calcined pellets of the Zr—Al carrier were evacuated at 50 mm Hg for a period of 0.5 hours, and the Dy—Li solution was then added. After a contact time of 1 hour, the pellets were separated from the solution, dried at 110° C. for a period of 12 hours and then calcined in air at 550° C. for 3 hours.

4.8 [g] $NH_4Cl$ were dissolved at room temperature in 15 $cm^3$ water. This solution was used, as described above, for the second impregnation of the Dy—Li—Zr—Al carrier.

TABLE 2

| Ex. # | Metals | | | | WHSV (LPG) ($h^{-1}$) | LPG Conversion (%) | Selectivity for $C_2$–$C_4$ olefins (%) |
|---|---|---|---|---|---|---|---|
| | X | Y | Z | Halogen | | | |
| 1 | Zr | Dy | Li | Cl | 6 | 75 | 62 |
| 2 | Zr | Dy | Li | Cl | 6 | 78 | 60 |
| 3 | Zr | Dy | Li | Cl | 4 | 62 | 74 |
| 4 | Ti | Dy | Li | Cl | 6 | 81 | 64 |
| 5 | Zr | La | Na | Br | 6 | 81 | 64 |
| 6 | Zr | Nd | Li | Cl | 6 | 65 | 71 |
| 7 | Ti | Pr | K | Cl | 6 | 59 | 82 |
| 8 | Zr | Dy | Li | I | 12 | 75 | 76 |
| 9 | Ti | Sn | Na | Cl | 6 | 49 | 53 |
| 10 | Zr | Sb | Li | Br | 6 | 46 | 68 |
| 13 | Zr | Dy | Li | Cl | 2 | 63 | 65 |

What is claimed is:

1. A catalyst composition comprising:

$X_aY_bZ_cA_dO_x$, wherein

X is Zirconium;

Y is at least one metal from the group of Lanthanides and Groups IVa and Va;

Z is at least one metal from Group I;

A is at least one halogen from Group VII;

O is oxygen;

and where
   a is in the range of 0.4 to 0.9;
   b is in the range of 0.005 to 0.3;
   c is in the range of 0.05 to 1.5;
   d is in the range of 0.05 to 0.8; and
   x is based on the valance requirements of the metals X, Y and Z as well as on the quantity of halogens.

2. The catalyst of claim 1, wherein
 a is in the range 0.5 to 0.8,
 b is in the range 0.01 to 0.2,
 c is in the range 0.1 to 1.0 and
 d is in the range 0.1 to 0.5.

3. The catalyst of claim 2 wherein the catalyst is deposited on a carrier material by:
 (a) dissolving in a solvent soluble components of the catalyst and impregnating the carrier material with the solution, so that the desired mole ratio of elements in the catalyst is obtained;
 (b) separating the solvent from the solution to obtain a moist catalyst;
 (c) drying the moist catalyst preferably at 110 to 150° C. over a period of 10 to 24 hours to obtain a dry catalyst;
 (d) calcining the dry catalyst from (c) at a temperature in the range of 250 to 600° C. for a period of 0.5 to 5 h; and
 (e) further calcining of the catalyst from (d) at a temperature in the range of 620 to 850° C. for a period of 10 to 24 hours.

4. The catalyst of claim 3 wherein at least one of the soluble components, a halogen component (A), is deposited onto the carrier material in separate steps prior to the further calcination.

5. The catalyst of claim 3 wherein the carrier material is at least one compound selected from the group consisting of silica, alumina, silicon carbide, silicon nitride, and oxides of the X or Y component, which is mixed with silica, alumina or silicon carbide as the binder.

6. The catalyst of claim 1 produced by the process comprising:
 (a) dissolving soluble components and dispersing insoluble components in a solvent in amounts to obtain the desired mole ratio of elements in the catalyst;
 (b) separating the solvent from the solution and obtaining a moist catalyst;
 (c) drying the moist catalyst at 110 to 150° C. over a period of 10 to 24 hours to obtain a dry solid;
 (d) crushing the dry solid of (c) to a powder, with a grain size in the range of 400 to 800 $\mu$m;
 (e) calcining the powder of (d) in an atmosphere that contains oxygen at a temperature in the range of 250 to 600° C., for a period of 0.5 to 5 h.
 (f) forming catalyst pellets from the powder of (e) by pressing and shaping into pellets with addition of moisture, surface-active substances and plastification or by extrusion with addition of a binder; and
 (g) calcining the formed pellets at a temperature in the range of 600 to 800° C. for 10 to 24 hours.

7. The catalyst of claim 6 wherein the calcined powder from (e), prior to forming is calcined additionally at a temperature in the range of 620 to 850° C. over a period of 10 to 24 hours.

8. The catalyst of claim 6 wherein the moist catalyst is dried in air or oxygen.

9. The catalyst of claim 1 wherein the active component of the catalyst is 10 to 90% by weight of the catalyst and the remainder is a carrier material.

10. The catalyst of claim 1 wherein the active component of the catalyst accounts for 10 to 90% by weight of the catalyst and the remainder is a binder.

11. The catalyst of claim 1 wherein Y is at least one metal selected from the group consisting of cerium, lanthanum, neodymium, dysprosium, tin, praseodymium, antimony and lead.

12. The catalyst of claim 1 wherein Z is at least one metal selected from the group consisting of lithium, sodium and potassium.

13. The catalyst of claim 1 wherein A is at least one halogen selected from the group consisting of chlorine, bromine and iodine.

14. A process for the oxidative dehydrogenation of paraffinic hydrocarbons that contain two to five hydrocarbon atoms to olefins comprising:
 contacting the hydrocarbons with a gas containing molecular oxygen and a dilution agent in a reaction zone over a catalyst of claim 1 at a temperature in the range of 400 to 700° C., a pressure in the range of 1 to 5 bar, a weight-relative space velocity (WHSV) of the paraffinic hydrocarbons in the range of 0.1 to 20 $h^{-1}$, a mole ratio of oxygen to the hydrocarbon in the range of 0.01 to 5 and a mole ratio of the dilution agent to the hydrocarbons in the range of 0.1 to 5.

15. The process of claim 14 wherein the temperature is in the range of 500 to 600° C.

16. The process of claim 14 wherein the WHSV is in the range of 5 to 7 $h^{-1}$.

17. The process of claim 14 wherein the pressure is in the range of 1 to 2 bar.

18. The process of claim 14 wherein the gas that contains oxygen is pure oxygen.

19. The process of claim 14 wherein the oxygen containing gas in introduced into the reaction zone in at least two stages.

20. The process of claim 14 wherein the paraffinic hydrocarbons are liquified petroleum gas.

21. The process of claim 20 wherein the paraffinic hydrocarbon is a mixture including propane, n-butane and isobutane.

22. The process of claim 14 wherein organic halogenides are present in the reaction zone.

23. The process of claim 14 wherein nitrogen is present in the reaction zone.

24. The process of claim 14 wherein the mole ratio of water vapor to the hydrocarbons is in the range of 0.1 to 4.

25. The process of claim 14 wherein the mole ratio of oxygen to the hydrocarbons is in the range of 0.01 to 1.0.

26. The process of claim 14 wherein the mole ratio of the halogens to the hydrocarbons is in the range of 0 to 0.01.

27. A calcined oxidic catalyst for the oxidative dehydrogenation/cracking of a paraffinic hydrocarbon which contains 2 to 5 carbon atoms to produce an olefin, the active component of the catalyst having a composition in accordance with the following formula:

$$X_a Y_b Z_c A_d O_x,$$

wherein
 X is Zirconium,
 Y is at least one metal selected from the group consisting of the lanthanides and IVa and Va,
 Z is at least one metal of Group I,
 A is at least one halogen of Group VII of the periodic system and O is oxygen,
and wherein
 a is a number in the range from 0.4–0.9,
 b is a number in the range from 0.005–0.3,
 c is a number in the range from 0.05–1.5,
 d is a number which depends on the valency requirements of the metals X, Y and Z and the quantity of halogens.

* * * * *